United States Patent [19]

Kosak

[11] Patent Number: 4,604,364

[45] Date of Patent: Aug. 5, 1986

[54] BIOLUMINESCENT TRACER COMPOSITION AND METHOD OF USE IN IMMUNOASSAYS

[76] Inventor: Kenneth M. Kosak, 3194 S. 4400 West, Salt Lake City, Utah 84120

[21] Appl. No.: 487,267

[22] Filed: Apr. 21, 1983

Related U.S. Application Data

[63] Continuation-in-part of Ser. No. 106,354, Dec. 21, 1979, which is a continuation-in-part of Ser. No. 430,921, Jan. 4, 1974, Pat. No. 4,000,252.

[51] Int. Cl.$^4$ .................. G01N 21/76; G01N 33/532; G01N 33/533; G01N 33/536
[52] U.S. Cl. ........................ 436/501; 435/8; 436/50; 436/56; 436/172; 436/544; 436/546; 436/800
[58] Field of Search ............... 435/8; 436/50, 56, 172, 436/501, 544, 546, DIG. 800

[56] References Cited

U.S. PATENT DOCUMENTS

| | | | |
|---|---|---|---|
| 4,104,029 | 8/1978 | Maier | 435/8 |
| 4,230,797 | 10/1980 | Boguslaski et al. | 435/7 |
| 4,246,340 | 1/1981 | Lundin et al. | 435/8 |
| 4,412,001 | 10/1983 | Baldwin et al. | 435/8 |

*Primary Examiner*—Herbert S. Cockeram
*Attorney, Agent, or Firm*—Richard F. Bojanowski

[57] ABSTRACT

A tracer composition is described whereby a nonradioactive photon emitter is coupled to a ligand, antigen or antibody for use in various immunoassay methods of analysis. The photon emitters employed are bioluminescent proteins such as firefly or bacterial luciferase as well as other luciferases from various species. To synthesize the new tracer, these photon emitters are coupled to antigens or antibodies using coupling agents such as glutaraldehyde, CNBr, carbodiimide and others. The coupling method may also include intermediate materials such as polysaccharides, polypeptides, polyacrylamides and others coupled between the photon emitter and the antigen or antibody.

Methods are described for using this tracer in both competitive and noncompetitive immunoassays to detect proteins, hormones, drugs, viruses and the like. Detection is accomplished by activating the tracer in a bioluminescent reaction and measuring the emitted light by photometric instruments or by photographic film. This new tracer composition has the advantages of nonradioactivity, high sensitivity and less endogeneous background activity.

25 Claims, No Drawings

BIOLUMINESCENT TRACER COMPOSITION AND METHOD OF USE IN IMMUNOASSAYS

RELATED PATENT APPLICATIONS

This application is a continuation-in-part of U.S. patent application Ser. No. 106,354, filed on Dec. 21, 1979, which in turn was a continuation-in-part of U.S. patent application Ser. No. 430,921, which was filed Jan. 4, 1974, and entitled Immunoscintillation Cell, now U.S. Pat. No. 4,000,252 the contents of both are hereby incorporated herein by reference. The inventor of the co-pending application and issued patent is the same as in the instant application.

BACKGROUND OF THE INVENTION

1. Field

This invention is directed to a composition and method for chemical analysis and particularly to a tracer composition comprising a nonradioactive photon emitter coupled to a ligand and its corresponding selective ligator or binding body.

2. State of the Art

The use of radioactive tracers with photon emitting materials for detecting and/or measuring organic materials is known as evidenced by the above referred to co-pending patent application. In that patent application an insolubilized or solid phosphor and binding body, such as an antibody, are associated by chemical or physical means to provide a solid scintillating imunoadsorbent composition. This composition is capable of selectively binding or retaining a radioactive labelled substance to a phosphor or photon emitting substance. The luminescence emitted by the phosphor is measured by a scintillation counter and is directly proportional to the radioactive energy released by the labeled antigen bound to the antibody that is coupled to the phosphor. A convenient means for combining a solid phosphor and/or binding agent is to covalently couple the binding body to the surface of the phosphor which is in bead form. Also, these beads could have ferrous metal or magnetic material included in their composition for magnetic manipulation during an assay.

A new radioactove tracer composition could be made by combining scintillating phosphors with a suitable polymeric substance and forming insoluble particles, beads or filaments a few microns in diameter. Included in their composition would be one or more insolubilized, radioactive isotopes which would constantly activate the phosphors within. Also, these particles could have ferrous metal or magnetic material included in their composition for magnetic manipulation during an assay.

The surface of these micro-particles could be derivatized or modified chemically so that specific antibodies (or antigens) could be covalently coupled to their surface. The resulting composition would be constantly scintillating particles with the specific binding properties of the antibody (or antigen) coupled to their surfaces. These particles could be used as a suspension of tracer particles in various competitive or noncompetitive radioimmunoassay methods.

Also, isotopes with different energies, such as $^3H$, $^{35}S$ and $^{14}C$ or different phosphors that emit distinguishable wavelengths could be used to produce tracer particles of different "colors". By coupling one type of antibody (or antigen) with particles of one color, they could be distinguished from particles of another color and antibody in the same suspension. In this way one or more substances could be assayed simultaneously in the same sample using a scintillation spectrophotometer.

Although the above patent application was directed primarily to the use of labeled antigens capable of transmitting radioactive energy to energize a photon emitting substance and thereby produce a measurable amount of luminescence; luminescence may also be produced by other means. For example, luminescence may be produced by chemical or biological means and does not require the use of radioactive energy. The resulting chemiluminescence or bioluminescence is capable of being measured by conventional measuring means such as a photometer, or by using photographic film.

In addition to radioactive tracers or radioactive induced luminescence, the literature discloses the use of fluorometric tracers for quantitatively and qualitatively measuring a chemical reaction.

A "tracer" is defined broadly as a material that is directly or indirectly detectable during or upon completion of a chemical or biological reaction. This is generally achieved by labelling an atom or molecule of one of the reactants used in the reaction. In a ligand binding reaction, a tracer is produced by combining a detectable substance with a ligand or ligator without adversely affecting its chemical or biological properties. Two major areas where ligand binding is employed are in chemical and clinical assays such as in immunoassays and in chemical separation assays as in chromatography.

Radioactive tracers have been used in "competitive" and "noncompetitive" assays wherein tracer-ligands are utilized in binding reactions and subsequently measured. The use of radioactive tracers was demonstrated in the above referred to co-pending patent application.

Fluorometric tracers have been used primarily in the form of fluorescent dyes wherein the dyes are absorbed or otherwise attached to a reactant. An incident light is then applied to activate the fluorescent product.

Although the use of radioactive and fluorometric materials as tracers are known, very little, if anything, can be found whereby a luminescent material is used as a tracer. One reason is that in the coupling of a luminescent material to a ligand, a coupling agent is usually needed. However, with certain radioactive and fluorescent tracers this combination can be achieved with relative ease.

With radioactive or fluorescent techniques, certain inherent disadvantages exist. For example, in using radioactive tracers, one disadvantage is that the isotopes used therein are inherently unstable since they are detected only when they disintegrate and therefore will make the tracer itself unstable. The highly active emitters are more desirable since they do not require highly sophisticated equipment to be detected as do the low energy emitters. However, the highly active emitters usually have shorter lifetimes, are more of a radiation hazard to workers and usually require stricter licensing for their use.

The disadvantage associated with fluorometric tracers is that the fluorometric tracers require an incident light source to activate the material. This contributes background interference which necessarily increases instrument complexity and expense in controlling this problem. In addition, certain filters or refraction gratings and quartz cells are normally required in order to measure the degree of energy being emitted.

Enzyme immunoassays are also well known wherein common enzymes such as oxidases, dehydrogenases and reductases have been used as labels for ligands. However, biological fluids such as human serum frequently contain enzymes with similar activity to the enzyme tracer being used. These serum enzymes can frequently be a source of troublesome background activity and require additional sample processing for their removal.

OBJECT OF THE INVENTION

It is, therefore, an object of this invention to provide a means of chemical analysis which avoids the disadvantages associated with the use of enzymatic, radioactive or fluorometric tracers. Another object of this invention is to provide a simple and economical means of chemical analysis. Another object of this invention is to provide a tracer composition whereby a ligand is coupled with a luminescent material. Still another object of this invention is to provide a ligand composition modified with a luminescent material without affecting its characteristic of selectively binding to a specific binding body. Other objects of this invention will be apparent from the disclosure which follows.

SUMMARY OF THE INVENTION

A tracer composition and method of chemical analysis is disclosed whereby a nonradioactive luminescent photon emitter is coupled to a ligand or antigen. This composition, although modified, possesses the same binding characteristics as the unbound or free ligand, and thus permits the tracer composition and free ligand to compete for its corresponding binding body or ligator. In the case where the ligand is an antigen, the ligator would be an antibody. The materials so bound can then be traced or quantitatively measured by energizing the photon emitting material without radioactivity or an incident light source and the primary photons released therefrom (in the form of light energy) can then be measured by photometric amplifying and measuring means.

DESCRIPTION OF THE PREFERRED EMBODIMENT

Throughout the specification and claims of this invention certain words, phrases and terms will be used. For purposes of this invention, it is intended that certain words, phrases and terms used herein have the following meaning:

Ligand

A ligand is defined as a selectively bindable material, that is bound by a specific binding body in a ligand binding reaction such as that which occurs between an antigen and an antibody. The interreaction between a ligand and protein-like types of specific binding bodies is well known in the art. Ligands are also capable of being bound to non-protein types of binding bodies such as chelators and surfactants. It is also known, as indicated above, that in immunological systems, the ligand would be the antigen, hapten or complement that would be bound by or to its antibody. In the case of an enzyme, a ligand would be the substrate or the coenzyme. Other substances that are capable of being bound by organic or biological bodies are proteins, hormones, vitamins, carbohydrates, lipids, lectins, interferons, antibiotics, drugs, pesticides, nucleic acids, microorganisms, blood cells and binding bodies used or modified such that they function as antigens.

Ligator or Specific Binding Body

Ligators or specific binding bodies can best be described functionally as being a specific substance or material or chemical that is capable of selectively binding with a ligand in a ligand binding reaction. A ligator can be a protein or a nonprotein binding body or a "specific reactor". When binding ligands, ligators would include antibodies, enzymes, plasma proteins, thyronine, intrinsic factor, globulins, biological receptors, chelators, surfactants, protein A, ribosome, RNA, DNA, cytochromes and lectins.

Luminescence

Generally, photon emission is electromagnetic radiation from molecules or atoms after they are excited and the electrons return to a lower energy state. Luminescence is defined as the product of a luminescent reaction. A luminescent reaction, for purposes of this invention, is defined as the production of nonradioactive primary light by means of the electronic excitation or ionization of molecules or atoms, without using an incident light source. Specifically this would include photons emitted through a chemical reaction like oxidation or ionization. It would also include certain physical or chemical techniques for electronic excitation that do not require an incident light source to cause photon emission. By definition, fluorescence, phosphorescence and radioactive photon emission would be excluded.

Luminescent Protected Photon Emitter

A luminescent protected photon emitter (hereinafter PPE) is defined as a scintillator that retains its luminescent activity in aqueous solutions. For purposes of this invention, a luminescent PPE should preferably fall within the following parameters:
  a. The PPE should be capable of luminescent in solutions of at least 80 percent water.
  b. The molecular efficiency of the luminescent reaction should be greater than or equal to 0.005. Molecular efficiency is defined as the number of photons emitted divided by the number of molecules excited. A more complete discussion on molecular efficiency can be found in Analytical Chemistry, Vol. 46, No. 2, p. 188A, February (1974), by Seitz & Neary entitled: "Chemiluminescence and Bioluminescence."

These parameters effectively exclude certain organic compounds which are potentially fluorescent, but have been made to emit photons under conditions generally unsuitable for biochemical assays employing biological substances, such as hormones, antibodies and enzymes.

Examples of chemiluminescent PPE include a number of cyclic compounds including cyclic hydrazides, peroxyoxalates, dioxetanes, indole-3-pyruvic acid, aryl Grignard reagents, riboflavin, lucigenin, luciferins, flavin mononucleotide, diazaquinone and isoquinoline and their respective derivatives.

Examples of bioluminescent PPE are the luciferase enzymes, as well as photoproteins, scintillons, lumisomes, certain metalloglycoproteins, and luciferin binding proteins including aequorin, mnemiopsin and berovin can also be used.

Conversely, a substance that inhibits photon emission could be used in an assay where reduction in light emission indicates the present of a tracer. For instance, an antibody that specifically bound and inactivated luciferase could be used as a label for a ligand or ligator. Also, an antibody that bound or inactivated a chemiluminescent substance like luminol could be used in a tracer composition.

Methods for Synthesizing Immunoscintillation Tracers

In the co-pending U.S. patent application, Ser. No. 430,921, filed Jan. 4, 1974, various methods were disclosed for attaching binding bodies such as antibodies or antigens to a scintillator which could be used as an insoluble immunoadsorbent. The same procedures and techniques disclosed therein can also be used in producing the coupled PPE-ligands of this invention. Although the terms ligand and/or ligator are used to described the binding entities, the use of a protected photon emitter in this invention is limited to photon emitters which are nonradioactive in nature. In addition, the product thereby produced can be used as a soluble tracer with an insoluble immunoadsorbent. With the latter, the regeneration techniques described in the co-pending application would be applicable.

The reagents that could be used in producing the conjugated PPE-ligand of this invention are those which will produce a product that will retain its binding properties and also its luminescent characteristics. Other factors such as simplicity of the synthesizing method, costs, availability of reagents, product solubility and ease of purification should also be considered.

The necessary ingredients which enter into the makeup of a ligand coupled to a protected photon emitter can be obtained by conventional methods such as that of entrapment, polymerizion, ionic or hydrogen bonding, hydrophobic bonding and covalent bonding.

For instance, a variety of potential labelling materials can be entrapped in microcapsules or in liposomes. Such labelling materials could be radioactive, fluorescent or enzymatic. Also, chemiluminescent materials such as luminol or bioluminescent luciferase could be entrapped by conventional methods described by T. M. S. Chang and G. Gregoriadis in "Methods in Enzymology" Vol. XLIV, Academic Press, N.Y. (1976).

A new tracer composition could be made by modifying the microcapsules or liposomes containing a luminescent material so that specific antibodies or antigens could be covalently coupled to their surfaces. These entrapped materials would then have the new property of specifically binding to a certain ligand or ligator, and could be used as tracers in various immunoassays. Also, these entrapped tracers could have ferrous metal or magnetic material incorporated into their composition for magnetic manipulation in an assay.

Because of its stability, covalent bonding usually is the preferred method and is widely used in the labelling of proteins and in conjugating haptens to carrier molecules for antibody production. Covalent bonding methods are also used for immobilizing antibodies, enzymes or ligands for immunological or enzymatic analysis as well as in affinity chromatography.

Functional Groups

Methods for covalent attachment make use of molecular functional groups found in organic and biochemistry. These would include the functional groups such as amines, amides, hydroxyls, carboxyls, carbonyls, sulfhydryls, indoles and others. When the necessary functional groups are not already on ligands, ligators and PPE's, they can be added through derivatization.

Many derivatized forms of certain ligands such as steriods are available commercially and derivatized forms of certain PPE's may be specially ordered through companies that will do custom synthesizing. Many methods intended for use in conjugating or immobilizing substances through crosslinking or coupling to solid supports would be applicable to attaching ligators and ligands to protected photon emitters. For example, many procedures that are intended for protein-like substances would also apply to ligands or ligators such as peptide hormones, viruses, enzymes and antibodies which are protein or protein-like in structure. Also, many protected photon emitters are protein-like in structure without modification. For example, luciferase, luciferase binding proteins, protein residue of aequorin, lumisomes and scintillons.

Coupling Agents

Depending on the functional groups on the ligand, specific binding body and protected photon emitter, various reagents or coupling agents are used to activate the functional groups and thereby promote the coupling of ligands and ligators with protected photon emitters. Examples of coupling agents are: glutaraldehyde, formaldehyde, cyanogen bromide, p-benzoquinone, succinic anhydrides, carbodiimides, epichlorohydrin, periodic acid, ethyl chloroformate, dipyridyl disulphide and azides, among others.

Table I, below, lists some known combinations of coupling agents and certain functional groups that can be found on various ligands, ligators and photon emitters.

TABLE I

| FUNCTIONAL GROUP ON LIGAND OR LIGATOR(R) | COUPLING OR CROSSLINKING AGENT | FUNCTIONAL GROUP ON PHOTON EMITTER(P) |
|---|---|---|
| a. R—NH$_2$<br>R—phenolic—OH<br>R—imidazole<br>R—SH$_2$ | glutaraldehyde[1,2] or aldehyde activated polypeptides[10] | P—NH$_2$ |
| b. R—COOH<br>R—NH$_2$ | carbodiimide[1,9,11] | P—NH$_2$<br>P—COOH |
| c. R—NH$_2$ | polyaldehydes[3,7] (periodate activated polysaccharide) | P—NH$_2$ |
| d. R—NH$_2$ | CNBr—polysaccharide[4,5,11] | P—NH$_2$ |
| e. R—NH$_2$<br>f. R—OH<br>R=NH<br>R=SH | polyacrylic azide[4,6]<br>p-benzoquinone[8,9] | P—NH$_2$<br>P=NH<br>P—OH |

References:
[1] Abraham, et al in "Principles of Competitive Protein Binding Assays", Odell and Daughaday, eds. Lippincott Co., Phil. (1971)
[2] Korn, et al, J. Mol. Biol. 65,525–529 (1972)
[3] Leemputten, et al, Biotech. 2nd Bioengin. XVI, 997–1003 (1974)
[4] Guilford, Chem. Soc. Rev. 2, 249–270 (1973)
[5] Jost, et al, Eur. J. Biochem. 48, 119–129 (1974)
[6] Erlanger, et al, Biochem. and Biophs. Res. Comm. 40, 70–76 (1970)
[7] Weliky, et al, Immunochemistry 2, 293–322 (1965)
[8] Ternynck, et al, Ann. Immunol. (Inst. Pasteur) 127C, 197–208 (1976)
[9] Mosbach, K. ed. "Methods in Enzymology" Vol XLIV, 11–148 (1976)
[10] Kurstak, et al, Ann. of the N.Y. Acad. of Sci. 254, 369–384 (1975)
[11] Weetal, Anal. Chem. 46, 602A–615A (1974)

Intermediate Soluble Support Materials

For instances where the ligand or ligator cannot be easily coupled directly to a protected photon emitter, an intermediate soluble support material may be used. A co-pending patent was directed primarily to the use of intermediate insoluble and immobilized support materials to which binding bodies and scintillators were coupled to produce an immunosorbent composition.

However, specific binding bodies, ligands and protected photon emitters can be coupled to low molecular weight, soluble or colloidal forms of support materials that are not immobilized and thereby produce an immunoscintillation tracer composition. These soluble or colloidal support materials are defined as intermediate soluble support materials for purposes of this invention. By coupling a ligand or ligator and a PPE to such an intermediate soluble support material, they would be covalently linked and therefore part of the same immunoscintillation tracer composition.

Examples of intermediate soluble support materials are proteins, polypeptides, polyaminoacids, polysaccharides, polyacrylamides, p-aminostyrenes, nylons, and low molecular weight, soluble or colloidal forms of various plastics, resins, silicas, metals, magnetic materials and other immunosorbent support materials. Some of the methods for coupling ligands and ligators to the photon emitter through a soluble support material are shown in Table I, a, c, d and e.

The feasibility of covalently coupling a protein-like PPE such as bacterial luciferase to the azide of polyacrylic acid while retaining its luminescent property has been demonstrated by Erlanger, B. F., et al in Biochem and Biophy, Res. Comm. 40, 70–76 (1970). Apparently, this coupling is through the free amine functional group found on the luciferase molecule. A ligand or ligator such as insulin or an antibody which also contains one or more free amines, can be coupled to a low molecular weight, soluble form of polyacrylic acid intermediate that luciferase is also coupled to and thereby produce a tracer composition. The feasibility of covalently coupling a PPE, flavin mononucleotide, to another compound while retaining its protected photon emitting properties in a bacterial bioluminescent reaction has also been demonstrated by Waters, C. A. in Biochem and Biophys. Res. Comm. 57, 1152–1158 (1974).

Other intermediate soluble support materials that can be used when both ligand and PPE have free amine functional groups are soluble proteins or polypeptides activitated with glutaraldehyde (Otto, H., et al, J. Immunol. Methods, 3, 137, 1973) or soluble dextran activated with cyanogen bromide (Jost, R., Eur. J. Biochem. 48, 119–129, 1974).

When certain ligands and PPE's cannot be conveniently coupled directly to each other, there are many proven methods for attaching such compounds through their functional groups to proteins, polypeptides or polyaminoacids. Such materials can be coupled to a corresponding PPE or ligand respectively, by methods that are generally used for protein-like compounds. For example, hapten-protein conjugates have been synthesized for producing antibodies to materials such as drugs, pesticides, indole compounds (Grota, L. J., et al, Can. J. Biochem. 52, 196–202, 1974) and steroids, (Rosenfeld, R. S., Steroids 21:5, 723–733, 1973).

Conditions such as reagent concentration, temperature, pH and reaction time would, of course, have to be determined empirically in order to obtain the most desirable tracer composition. These synthesizing conditions must be such that the immunoscintillation composition produced can function as a bindable tracer, that is, retain its optimal binding and luminescent properties.

The example to follow reacts a functional group such as a free amine located on a protected photon emitting material with a ligand whereby the resulting product retains both its bioluminescent and ligator binding properties. In this example, the coupling agent is glutaraldehyde. Luciferase was used as the protected photon emitting material coupled to the ligand as it possesses free amines which are not essential to the luminescent reaction.

In the example to follow, a method of analysis is demonstrated whereby luciferase is used in the luminescent tracer in an assay to measure immunogobulin G and immobilized antibody is used in the separation step. It has been found that with certain modifications of the technique set forth below, other proteins may likewise be measured.

EXAMPLE I

Competitive Binding Assay for Human IgG (a) Preparation of Immunoscintillation Tracer Using Luciferase In 0.1 ml of 0.05M phosphate buffered saline, pH 7.0, (hereinater PBS), containing approximately 0.5 mg of human immunoglobulin G. (hereinafter IgG), (Sigma Chemical Co.) was added approximately 1.5 mg of bacterial luciferase (Sigma) in a 0.2 ml of PBS, purified by the method of Gunsalus-Miguel, A., et al, J. Biol. Chem. 247, 398–404 (1972). A few microliters of glutaraldehyde (VWR Scientific) was added to give a final concentration of 0.2%. The solution was gently agitated at approximately 4° C. and then diluted with 1 ml PBS before precipitation occurs or after 1 to 2 hours and dialyzed against PBS overnight at 4° C.

Based on the desired luminescent and binding activity, the tracer concentration was adjusted by dialysis against polyethylene gylcol to concentrate and/or diluted with PBS containing 0.2% bovine serum albumin, (hereinafter BSA), (Sigma) and 0.02% sodium azide. The concentration of tracer solution was determined by measuring the luminescence of 0.1 ml of tracer solution in 1.9 ml of PBS containing 0.2% BSA by the procedure set forth in paragraph (d), below.

One tenth of the adjusted tracer solution was then used in the blank reaction as set forth in paragraphs (b) and (c). The blank luminescence was determined with procedures set forth in paragraphs (d) and (e). By running three or more of each test, mean values for the total and blank luminescence can be determined. The blank percent bound was then determined by dividing the mean blank luminescence by the mean total luminescence and multiplying by 100. The blank percent bound indicates the degree of binding activity of the tracer. Preferably, the binding activity should be from 30 to 100 percent depending on assay conditions.

(b) Ligand Binding Reaction

The optimum concentrations of tracer and antibody can be determined empirically through a "blank" ligand binding reaction. This permits a significant and consistent amount of tracer to be bound by the antibody in the absence of a competing ligand. In the blank reaction, all conditions are identical to those which would normally be used in running a sample except that the sample is replaced with an equal volume of the assay buffer. The blank reaction establishes a "zero" concentration to which the unknown samples may be compared.

The necessary dilutions of tracer, anti-human IgG (Antibodies Inc.), and sample solutions were made with an assay buffer containg PBS, pH 7.0, and 0.2% BAS. The reaction was run by combining 0.1 ml of each of these solutions following a standardized procedure. Assay buffer was substituted for the sample when running a blank reaction. In a suitable container, the reagents were mixed and incubated at a temperature that will not cause reagent degradation, suitably 4°-25° C. This temperature allows the reaction to approach equilibrium which normally takes between 2-12 hours. The free and/or bound fractions of tracer are then separated and measured for luminescent activity. To separate bound and free tracer, 0.2 to 0.3 ml of the incubation volume was applied to an immunosorbent column as described in paragraph (c). Luminescence of the antibody bound tracer in the filtrate was determined by the bioluminescent reaction described in paragraphs (d) and (e). This is called the bound samples luminescence. Through repeated testing of the samples, (three or more of each), their mean luminescent values can be determined as with the total luminescence described in paragraph (a).

The sample percent bound was determined by dividing the mean sample luminescence by the mean total luminescence and multiplying by 100. When the sample percent bound was significantly less than the blank percent bound and outside of their mean deviations, then it was concluded that the sample contained a ligand that is competitive with the tracer. In most cases, the difference will be greater than or equal to 5 percent. Depending on antibody specificity and controls to account for interfering substances, the above indicates that the competing sample ligand was identical to the ligand of the tracer which in this case was human IgG. Conversely, if the sample percent bound was significantly more than the blank percent bound then it may be concluded that the sample contained ligand binding bodies, such as anti-human IgG.

(c) Separation on Immunosorbent Column

The immunosorbent was prepared by immobilizing 0.5 ml of anti-human IgG serum (Antibodies Inc.) on 5 gm of CNBr activated sepharose 4B (Pharmacia Fine Chemicals) according to manufacturer's directions so that the antibodies remained functional. Chromatography columns with bed volumes of 2.0 ml equlibrated with assay buffer containing 0.02% sodium azide were prepared for each sample.

Before the sample was introduced, the column was allowed to drain and excess liquid was forced out of the column with air. The sample was then introduced into the column and permitted to stand for five (5) minutes. The filtrate was collected in a single tube by introducing assay buffer in aliquots of 0.3 ml until the sample fraction not bound by the immunosorbent was collected. Depending on column characteristics, 6 aliquots of 0.3 ml are normally required. However, the column should be allowed to drain before applying each aliquot. The collected sample filtrate is now ready for determining the amount of antibody bound tracer present by its luminescent activity.

Under different conditions, the tracer fraction bound to the immunosorbent may be measured by using it in a luminescent reaction before or after elution. The immunosorbent may then be regenerated and resued as in an automated, continuous flow system. Other methods of separating the bound and free fractions may also be employed such as by double antibody, salt or solvent precipitation, as well as the use of immunosorbents or adsorbents in a batch procedure.

(d) Bioluminescent Reaction

Two ml of the unknown sample are added to 0.5 ml of assay buffer containing an amount of flavin mononucleotide, (hereinafter FMN), (Sigma), sufficient to allow saturation of the luciferase, (i.e., a $1 \times 10^{-4}$ molar concentration). About 0.5 to 1.0 mg of solid sodium dithionite (Fisher Chemical) is added to maximally reduce the FMN present to $FMNH_2$, without causing a decrease in luminescence. The reduction of FMN can be determined empirically in separated tests by monitoring for the loss of FMN fluorescence, excited at 525 mn, in the above mixture. The luminescent reaction is initiated by injecting 1 ml of aerated, oxygen equilibrated distilled water containing 0.1% (V/V) decaldehyde (Sigma) in suspension.

(e) Luminescence Detection

Luminescence detection was accomplished with a photometer such as the Aminco Fluor-Colorimeter with no filters and the incident light source turned off. Depending on the sensitivity desired, machine stability and luminescent activity of the sample, adjustments are made according to manufacturer's directions to minimize noise and subtract background. Suitably, the sensitivity scale is set at 0-3, 0-1 or 0-0.3.

The light emitting reaction was performed in a cuvette in the detector with a reflective surface such as silvered Mylar on the side opposite the one facing the photomultiplier tube. A lower background and higher sensitivity is obtained by detecting the reaction in a partially darkened room or with an appropriate light cover over the cuvette that facilitates injection of reagents. Alternatively, the reactions may be detected in a flow cell or coil where the necessary reactants are brought together via tubing arrangements and controlled by an automated or semi-automated device.

A strip chart or digital recorder is convenient for recording the luminescent reactions. Under different conditions, luminescent tracer reactions may be measured and recorded by exposing photographic film to the reaction. The luminescent tracer may expose the film remotely or as part of the film's reactive coating when a sample is applied to it.

(f) Preparation of a Standard Curve

Depending on the test requirements, samples may simply be compared with "blank" samples to determine the presence of the analyte. A standard curve may be desired for more precise quantitation.

Prepare standard solutions in PBS, pH 7.0, containing 0.2% BSA and 0.02% sodium azide with final concentrations of 0, 0.01, 0.1, 10 and 100 micrograms per ml of human IgG (Sigma). Depending on assay conditions, other concentration ranges or increments may be used.

In preparing the standard curve, the runs preferably should be made in triplicate. For each run, 0.1 ml of each standard solution is run through procedures set forth in paragraphs (b), (c), (d) and (e) in place of the blank or sample as described. Calculate the standard percent bound for each by dividing the mean standard luminescence by the mean total luminescence and multiply by 100. Plot the standard percent bound versus the known concentration per ml to produce a standard curve. The concentration of an unknown sample is equal to the concentration that coincides with the sample percent bound read on the standard curve.

The example to follow reacts a functional group such as a free amine located on the PPE, luminol, with a ligator, anti-human IgG antibody, whereby the resulting composition retains both its chemiluminescent and ligand binding properties. The coupling agent is glutaraldyhde. A method of analysis is demonstrated whereby a luminescent tracer is used with an immobilized antigen.

EXAMPLE II

"Sandwich" Assay for Human IgG (a) Preparation of Immunoscintillation Tracer Using Luminol In a 0.5 ml solution of PBS (phosphate buffered saline) containing approximately 0.5 mg of antibody raised against human IgG (Antibodies Inc.), approximately 1 ml of 0.02M luminol (Sigma) in 0.1M sodium bicarbonate solution, pH 8-9 was added. To this solution, a few microliters of glutaraldehyde were added to give a final concentration of 0.1 to 0.2%. The mixture was agitated gently at approximately 4° C. and 0.5 ml of aqueous 1M 2-aminoethanol adjusted to pH 7.5 was added before precipitation occurred or after 1 to 6 hours. Then it was dialyzed for 4 hours against PBS containing 0.1M 2-aminoethanol, pH 7.5 and then dialyzed overnight against PBS at 4° C. If any precipitate formed, it was centrifuged and the supernatant used. The necessary reaction time and reagent concentrations are determined empirically to give optimal coupling of the luminol to the protein without causing excessive precipitation.

Based on the desired luminescent and binding activity, the tracer concentration was adjusted by dialysis against polyethylene glycol to concentrate, and/or diluted with PBS containing 0.2% BSA and 0.02% sodium azide. The concentration of the tracer was adjusted so that the total luminescence value is in the upper range of the detection scale selected on the photometer. The total luminescence was determined by measuring the luminescence of 0.5 ml of tracer solution in 0.5 ml of distilled water as set forth in paragraph (b) of this example and detected as set forth in paragraph (e) of example 1.

(b) Chemiluminescent Reaction

The 2 ml sample to be measured was added to a cuvette containing 1 ml of 1M borate buffer, pH 11, (prepared by adding approximately 15 ml of 1M potassium hydroxide to 25 ml of 1M boric acid.) Then 0.2 ml of 0.025% cobaltous acetate (Sigma) in water was added and mixed. With the detection device prepared and the cuvette suitably positioned and/or covered to reduce exposure to outside light, the luminescent reaction was initiated by quickly injecting 0.3 ml of 1M aqueous hydrogen peroxide into the cuvette with suspended sample.

(c) Preparation of Immunosorbent

Approximately 0.5 ml of anti-human IgG (Antibodies Inc.) was immobilized on 5 gm of CNBr activated sepharose 4B (Pharmacia) and the gel washed according to manufacturer's directions so that the antibodies are still functional. The gel was suspended in 50 ml of assay buffer, which is PBS, pH 7.0, containing 0.2% BSA and 0.02% sodium azide.

(d) Ligand Binding "Sandwich" Reaction

The purpose of the reaction is to expose the polyvalent antigen of the sample to an excess of antibody on a solid support so that essentially all antigen is bound to the antibody. Then a sufficient amount of luminescent tracer antibody is added so that it binds in "sandwich" fashion to all of the antigen bound to the immunosorbent. After the excess tracer is removed, the remaining bound tracer is determined by a luminescent reaction. If no tracer is bound to the immunosorbent, then it can be inferred that no antigen was in the sample initially.

Depending on immmunosorbent and tracer activity, the optimum concentrations of immunosorbent and tracer for a given range of sample antigen concentrations can be determined empirically. A standard sample was used containing an antigen concentration in the upper limits of the desired range. This is called the standard reaction.

Preferably, 0.5 ml of sample containing 1 to 100 micrograms of human IgG (Sigma) was added to 0.2 ml of settled and decanted immunosorbent gel, representing an excess of antibody. This mixture was allowed to incubate long enough to allow binding of the antigen, preferably 2-12 hours, at a temperature that facilitates binding without excessive reagent degradation, preferably 4°-25° C.

The immunosorbent was then washed with 2 ml of assay buffer, centrigued and decanted. Tracer solution was added to give an excess of tracer over bound antigen, preferably in a volume of 0.5 ml. This was allowed to incubate until sufficient binding occurred as with the first incubation. The immunosorbent was then washed with 2 ml of assay buffer, centrifuged, decanted and suspended in 1 ml of distilled water.

Then the standard luminescence was determined for the 1 ml sample as set forth in paragraph (b) of this example and paragraph (e) of Example 1. The standard percent bound was calculated by dividing the standard luminescence by the total luminescence and multiplying by 100. This indicates the binding activity of the tracer and immunosorbent and generally is from 30 to 100 percent, depending on assay conditions.

Through the various synthesis methods described above, other PPE's can be substituted for those used in Examples I and II. However, the basic assay procedures would be similar except for variations in operating conditions to obtain luminescence with the particular PPE used.

For example, when firefly luciferase is substituted for bacetrial luciferase in Example I, the luminescent reaction would require the presence of luciferin, ATP, oxygen and magnesium ion or suitably substitutes for these reagents (Hammerstedt, R. H., Anal. Biochem. 52, 449-455, 1973, and Zinner, K., Biochem. and Biophys. Res. Comm. 61, 889-898, 1974). Other examples of PPE's that may be substituted for bacterial luciferase with references for their luminescent reactions are: photoproteins (Ward, W. W., Proc. Nat. Acad. Sci. USA, 72, 2530-2534, 1975), luminosomes, (Henry, J. P., Biochem and Biophys. Res. Comm. 62, 253-259, 1975), scintillons and dinoflagellate luciferases (Schmitter, R. E., J. Cell. Physiol. 87, 123-134, 1976) and mollusc luciferase (Henry, J. P., Biochem. 14, 3458-3466, 1975), among others.

Although Examples I and II demonstrate specific embodiments of this invention employing bioluminescent and chemiluminescent PPE's, respectively, other uses for the compositions herein disclosed would be readily available.

For example, the immunoscintillation tracer composition could be used in other types of ligand binding assays such as heterogeneous and homogeneous ligand binding assays, competitive and non-competitive assays as well as batch, continuous and automated systems employing the ligand or ligator binding concept. Adapting the composition disclosed herein for chromatographic use could be readily achieved.

In each instance various modifications in operating parameters may be required to achieve optimal operating potential. Such conditions, however, would be readily available to one skilled in the art.

While the invention has been described with reference to certain specific embodiments, it is understood that changes may be made by one skilled in the art and it would not thereby depart from the spirit and scope of the invention which is to limited only by the claims appended hereto.

Pertinent References

The following is a list of articles pertinent to the technology recited above:
Blauer, G., FEBS Letters 54, 1–4 (1975)
Cormier, M. J., et al, ed., Chemiluminescence and Bioluminescence, Plenum Press, N.Y. (1973)
Hastings, J. W. et al, Photochem. and Photobiol. 23, 461–473 (1976)
Lee, J., Photochem. and Photobiol. 20, 535–539 (1974)
Nord, F. F., ed., Advances in Enzymology, XXV, pp.119–166, Interscience, N.Y. (1963)
Schroeder, H. R., et al, Anal. Biochem. 72, 283–292 (1976)
Schroeder, H. R., et al, Anal. Chemistry. 48, 1933-1937 (1976)
Seliger, H. H., Photochem. and Photobiol. 21, 355–361 (1975)
Song, P-S., Photochem. and Photobiol. 18, 531–534 (1973)
Song, P-S, Photochem. and Photobiol. 20, 527–532 (1974)
Stanley, P. E., et al, ed., Liquid Scintillation Counting: Recent Developments, pp. 383–430, Academic Press, N.Y. (1974)

I claim:

1. A tracer composition comprising a material to be labelled selected from the group consisting of ligands and ligators, covalently coupled to luciferase through functional groups that are capable of coupling with glutaraldehyde, such functional groups being selected from amine, amide, phenolic hydroxyl, carbonyl and sulfhydryl groups.

2. The composition of claim 1, wherein said ligator is an antibody.

3. The composition of claim 1, wherein said ligand is an antigen.

4. The composition of claim 1, wherein said tracer composition includes an intermediate soluble support material such as proteins, polypeptides, polysaccharides, polyacrylamides and polyaldehydes through which said material to be labelled and said luciferase are covalently coupled.

5. The composition of claim 1, wherein said ligator is protein A.

6. The composition of claim 1, wherein said luciferase is selected from the group consisting of bacterial luciferase, firefly luciferase, coelenterate luciferase, crustacean luciferase, annelid luciferase, molluscan luciferase and dinoflagellate luciferase.

7. The composition of claim 1, wherein said ligator is primarily protein material selected from the group consisting of proteins, enzymes, intrinsic factor, globulins, biological receptors, ribosomes, cytochromes and lectins and wherein said material, or a derivative thereof, has ligand binding properties and the necessary functional groups for coupling.

8. The composition of claim 1, wherein said ligator is primarily non-protein material selected from the group consisting of steroids, RNA, and DNA and wherein said material, or a derivative thereof, has ligand binding properties and the necessary functional groups for coupling.

9. The composition of claim 1, wherein said ligand is primarily protein material selected from the group consisting of proteins, complement, hormones, interferons, viruses, microorganisms and blood cells and wherein said material, or a derivative thereof, has ligator binding properties and the necessary functional groups for coupling.

10. The composition of claim 1, wherein said ligand is primarily non-protein material selected from the group consisting of haptens, coenzymes, carbohydrates, lipids, antibiotics, drugs, pesticides and nucleic acids and wherein said material, or a derivative thereof, has ligator binding properties and the necessary functional groups for coupling.

11. The composition of claim 1, wherein said ligand is a vitamin of the B group, such as pyridoxines, or of the D group, such as calciferols, or vitamin H, such as biotin, or of the K group such as naphthoquinones and wherein said vitamin or a derivative thereof, has ligator binding properties and the necessary functional groups for coupling.

12. A tracer composition comprising an antibody covalently coupled to luciferase through functional groups that are capable of coupling with glutaraldehyde.

13. A tracer composition comprising a material to be labelled selected from the group consisting of ligands and ligators, covalently coupled to a bioluminescent photon emitter selected from the group consisting of photoproteins, aequorin, mnemiopsin, berovin, scintillons and lumisomes.

14. The composition of claim 13, wherein said tracer composition includes an intermediate soluble support material such as proteins, polypeptides, polysaccharides, polyacrylamides and polyaldehydes through which said material to be labelled and said bioluminescent photon emitter are covalently coupled.

15. The composition of claim 13 wherein said ligator is an antibody.

16. The composition of claim 13 wherein said ligand is an antigen.

17. In a nonradioactive immunoassay method for determining the presence of ligands and ligators in a competitive assay comprising
(1) bringing together under conditions conducive to binding;
(a) said ligand to be measured, with;
(b) a ligator which has selective affinity for (a) and where the concentration of (b) is not sufficient to bind all of (a), with;
(c) a labelled ligand which has selective affinity for (b) and competes with (a) for binding to (b);

(2) and selectively determining the amount of unbound (c) and of (c) bound to (b);

the improvement wherein said labelled ligand is a bioluminescent tracer composition comprising a material selected from the group consisting of ligands and ligators covalently coupled to luciferase and wherein step 2 includes the use of a bioluminescent reaction for detection.

18. In a nonradioactive immunoassay method for determining the presence of ligands and ligators in a noncompetitive "sandwich" assay comprising
(1) bringing together under conditions conducive to binding;
 (a) said ligand to be measured, with;
 (b) an insolubilized ligator which has selective affinity for (a) and where the concentration of (b) is sufficient to bind all of (a) noncompetively, with;
 (c) a labelled ligator which has selective affinity for (a) but not (b) and;
(2) selectively determining the amount of (c) bound to (a) and of unbound (c);

the improvement wherein said labelled ligator is a bioluminescent tracer composition comprising a material selected from the group consisting of ligands and ligators covalently coupled to luciferase and wherein step 2 includes the use of a bioluminescent reaction for detection.

19. The method of claim 17 or 18, wherein said selective determination of step 2 includes exposing photographic film to the light emitted from said bioluminescent reaction.

20. In a nonradioactive assay method for determining the presence of ligands and ligators in a competitive binding assay comprising,
(1) bringing together under conditions conducive to binding;
 (a) said ligand to be measured with;
 (b) a ligator which has selective affinity for (a) and where the concentration of (b) is not sufficient to bind all of (a), with;
 (c) a labelled ligand which has selective affinity for (b) and competes for binding to (b);
(2) and selectively determining the amount of unbound (c) and of (c) bound to (b);

the improvement wherein said labelled ligand is a bioluminescent tracer composition comprising a material selected from the group consisting of ligands and ligators covalently coupled to a bioluminescent photon emitter selected from the group consisting of photoproteins, aequorin, mnemiopsin, berovin, scintillons and lumisomes and wherein step 2 includes the use of a bioluminescent reaction for detection.

21. The method of claim 20, wherein selective determination of step 2 includes exposing photographic film to the light emitted from said bioluminescent reaction.

22. In a nonradioactive assay method for determining the presence of ligands and ligators in a noncompetitive "sandwich" assay comprising,
(1) bringing together under conditions conductive to binding;
 (a) said ligand to be measured with;
 (b) an insolubilized ligator which has selective affinity for (a) and where the concentration of (b) is sufficient to bind all of (a) noncompetitively, with;
 (c) a labelled ligator which has selective affinity for (a) but not (b) and
(2) selectively determining the amount of (c) bound to (a) and of unbound (c);

the improvement wherein said labelled ligator is a bioluminescent tracer composition comprising a material selected from the group consisting of ligands and ligators covalently coupled to a bioluminescent photon emitter selected from the group consisting of photoproteins, aequorin, mnemiopsin, berovin, scintillons and lumisomes and wherein step 2 includes the use of a bioluminescent reaction for detection.

23. The method of claim 22, wherein selective determination of step 2 includes exposing photographic film to the light emitted from said bioluminescent reaction.

24. In a nonradioactive assay method for determining the presence of ligands and ligators in a noncompetitive "sandwich" assay comprising,
(1) bringing together under conditions conducive to binding;
 (a) said ligand to be measured with;
 (b) an insolubilized ligator which has selective affinity for (a) and where the concentration of (b) is sufficient to bind all of (a) noncompetitively, with;
 (c) a labelled ligator which has selective affinity for (a) but not (b) and
(2) selectively determining the amount of (c) bound to (a) and of unbound (c);

the improvement wherein said labelled ligator is a chemiluminescent tracer composition comprising a material selected from the group consisting of ligands and ligators covalently coupled to a chemiluminescent material selected from the group consisting of luminol, lucigenin, cyclic hydrazides, peroxyoxalates, dioxetanes, diazaquinone and their respective derivatives and wherein step 2 includes the use of a chemiluminescent reaction for detection.

25. The method of claim 24, wherein selective determination of step 2 includes exposing photographic film to the light emitted from said chemiluminescent reaction.

* * * * *